(12) United States Patent
Lendl

(10) Patent No.: US 6,737,651 B1
(45) Date of Patent: May 18, 2004

(54) METHOD OF INFRARED-OPTICALLY DETERMINING THE CONCENTRATION OF AT LEAST ONE ANALYTE IN A LIQUID

(75) Inventor: Bernhard Lendl, Vienna (AT)

(73) Assignee: Innovationsagentur Gesellschaft m.b.H., Vienna (AT)

( * ) Notice: Subject to any disclaimer, the term of this patent is extended or adjusted under 35 U.S.C. 154(b) by 0 days.

(21) Appl. No.: 09/958,248

(22) PCT Filed: Apr. 7, 2000

(86) PCT No.: PCT/AT00/00084
§ 371 (c)(1),
(2), (4) Date: Oct. 5, 2001

(87) PCT Pub. No.: WO00/62040
PCT Pub. Date: Oct. 19, 2000

(30) Foreign Application Priority Data

Apr. 7, 1999 (AT) .............................. 616/99

(51) Int. Cl.$^7$ .............................. G01N 21/59
(52) U.S. Cl. .............. 250/343; 250/338.5; 250/339.12
(58) Field of Search .............. 250/343, 338.5, 250/339.12

(56) References Cited

U.S. PATENT DOCUMENTS

| | | | |
|---|---|---|---|
| 5,268,910 A | | 12/1993 | Huber |
| 5,331,409 A | * | 7/1994 | Thurtell et al. .............. 356/437 |
| 5,746,942 A | | 5/1998 | Bowman et al. |
| 5,838,869 A | | 11/1998 | Rasch et al. |
| 5,901,168 A | | 5/1999 | Baillargeon et al. |
| 5,922,609 A | * | 7/1999 | Kellner et al. .............. 436/103 |
| 6,161,028 A | * | 12/2000 | Braig et al. .............. 600/316 |

FOREIGN PATENT DOCUMENTS

| | | |
|---|---|---|
| AT | 404 514 B | 12/1998 |
| GB | 1 521 085 | 8/1978 |

OTHER PUBLICATIONS

WO 92/17767, Method for Quantitative Determination of Fat in an Emulsion which Contains Fat Particles, Publication Date: Oct. 15, 1992.

* cited by examiner

Primary Examiner—Constantine Hannaher
Assistant Examiner—Timothy Moran
(74) Attorney, Agent, or Firm—Rankin, Hill, Porter & Clark LLP

(57) ABSTRACT

Disclosed is a method of infrared-optically determining the concentration of at least one analyte in a liquid sample, wherein the infrared absorption of the analyte(s) is measured and compared with a standard, which is characterized in that the liquid sample is sampled with an infrared radiation of high light density, wherein the infrared radiation has a sharp intensity peak at at least one wave length, as well as an arrangement for the infrared-optical transmission determination of the concentration of at least one analyte in a liquid sample, with a sample cuvette flowed through by the sample liquid, the sample cuvette being arranged in the radiation path between a radiation source for providing the infrared radiation and a detector for measuring the infrared absorption induced by the analyte in the sample cuvette.

17 Claims, 9 Drawing Sheets

METHOD OF INFRARED-OPTICALLY DETERMINING THE CONCENTRATION OF AT LEAST ONE ANALYTE IN A LIQUID

BACKGROUND OF THE INVENTION

The invention relates to a method of infrared-optically determining the concentration of at least one analyte in a liquid sample, wherein the infrared absorption of the analyte is measured and compared with a standard.

The invention further relates to a device for the infrared-optical transmission determination of the concentration of at least one analyte in a liquid sample, with a sample cuvette filled with the sample liquid, the sample cuvette being arranged in the radiation path between a radiation source for providing the infrared radiation and a detector for measuring the infrared absorption induced by the analyte in the sample cuvette.

Moreover, the invention relates to the use of such an arrangement for the infrared-optical transmission determination of the concentration of at least one analyte in a liquid sample.

The detection or measurement of concentration of substances in a sample is performed in many scientific and technological fields, e.g. chemistry, process technology, production technology, medical technology, environmental analytics, and food analytics, by means of absorption spectra. The infrared spectrum is particularly suitable, since precisely in this range many analytes have characteristic absorption bands from the intensity of which the analyte concentration can be determined.

GB 1 521 085 A discloses a detector for an infrared analyzer, which serves to determine the concentration of a certain component in a liquid or gaseous sample. A filter that passes infrared radiation of a single narrow wavelength range is placed between the sample cuvette and the radiation source. A wavelength range is chosen which is absorbed by the substance to be analyzed. By the difference between the absorption spectra of the sample with analyte and the sample without analyte, the presence as well as the concentration of the analyte in the sample can be determined. This described analyzer, however, requires a complicated arrangement, and the results obtained are not sufficiently specific.

WO 921/7767 relates to a method for quantitating fat in a fat-particle-containing emulsion by using infrared absorption techniques, wherein the absorption peak at a wavenumber of approximately 1160–1190 $cm^{-1}$ is used for determining the fat concentration.

AT 404,514 B describes a further arrangement for measuring analytes in a liquid sample by infrared absorption. Before the measurement, the analyte to be measured is subjected to a chemical reaction which leaves all the remaining components of the liquid sample unaffected, and the change in the infrared absorption caused by the chemical reaction with the analyte is measured as a function of the analyte concentration to be determined. This chemical reaction is, e.g., a change of the pH, so that the substance to be analyzed is present in a certain form before the pH change, such as a single-charged substrate or an uncharged phosphoric acid which is non-absorbing or only slightly absorbing at the wavelength indicated. After the pH change, the analyte is present in a form, e.g. triple-charged phosphate, which has an absorption maximum at the wavelength indicated. From the difference of measurement before and after the chemical reaction, the presence and the concentration of the analyte can be determined. To produce light with a certain wavelength, a filter that passes infrared radiation of a single narrow wavelength range is placed between the sample cuvette and the source of radiation. This method is simple and rapid, yet in view of the described chemical reaction, includes difficulties as regards the sensitivity and robustness of the analyzer.

It also is known in the art that a selective concentration determination of glucose in complex mixtures such as human serum, is possible by absorption measurement at a few wavelengths in the middle region of the infrared spectrum, as described by Heise et al. in Fresenius J. Anal. Chem. (1997), 359, 93–99. Absorption spectra in the middle of the infrared spectrum were taken on blood plasma and whole blood samples using a Fourier Transform Infrared (FT-IR) spectrometer. Heise et al. also disclosed a chemometric model for the determination of glucose in unknown samples, where a few wavelengths were sufficient to obtain results equal to, or better than, results obtained by means of a PLS (partial least square) model covering the entire (1200–950 $cm^{-1}$) spectral range. A drawback of this method is, however, that the FT-IR spectrometer is not handy and is heavy and the employed measurement on the surface of a toxic ZnSe crystal is not usable for on-line determinations of biological samples in so far as the samples, due to the contact with the toxic ZnSe crystal, also become toxic after the determination. Moreover, there are potential problems with the absorption of proteins on the surface, and, lastly, transmission measurements in practice cannot be made since the FT-IR spectrometer, which has a low light intensity, only allows for the use of layers only up to 50 micrometers thick. Such layer thicknesses, however, are not suitable particularly when determining the concentration in biological samples, since within a short time the thin layer will be clogged or the sample (e.g. whole blood) will be damaged, whereby an on-line measurement, e.g. on the living patient, with a return of the sample to the patient becomes life-threatening and thus completely impossible.

In general, conventional radiation sources for producing infrared radiation are based on thermic radiators and accordingly are limited in their radiation power. Thus, the radiation power emitted by a thermic radiator of 1500 K in the narrow spectral range of from 9.9 to 10.1 $cm^{-1}$ is less than 0.2% of the entire radiation power emitted. Due to the practical difficulties of efficiently collecting emitted radiation, only a small fraction of the emitted radiation is actually available for the measurement. For example, a state of the art spectrometer from Bruker GmbH, the radiation power distributed over the entire region of the spectrum and finally available in the sample chamber is only approximately 25 mW. The consequence thereof is that in the narrow wavelength range from 9.9 to 10.1 $cm^{-1}$, only low power, approximately 50 $\mu W$, is available. With respect to the thermic radiator as disclosed in AT 404,514, it is estimated that the usable power is only in the range of approximately 100 $\mu W$.

SUMMARY OF THE INVENTION

Thus, it is an object of the present invention to provide a method as well as an arrangement for the infrared-optic transmission determination of the concentration of an analyte in a liquid sample, which can be carried out easily and rapidly, has a sufficient sensitivity and robustness so as to afford a marketable product, and which, in particular, is suitable for on-line measurement of biological samples where the sample is returned to the patient.

The method is characterized in that the liquid sample is irradiated with infrared radiation of high light density, wherein the infrared radiation has a sharp intensity peak at at least one wavelength.

Such infrared radiation with a high power density is produced with a laser, wherein, due to the high spectral density and the sharp intensity peaks with lasers, spectroscopic methods are possible, which cannot be carried out with conventional radiation sources. The combination of the [infrared] spectroscopy with laser spectroscopy results in a method for infrared-optic transmission determination of analytes in a liquid sample, which has a markedly higher sensitivity, flexibility and robustness than conventional methods.

With the method according to the invention, concentrations of ions as well as any other substances, such as organic acids, in particular fatty acids, alcohols, carbohydrates, in particular glucose, proteins, urea etc. can be measured with high precision.

BRIEF DESCRIPTION OF THE DRAWINGS

FIG. 3 shows the voltage-time diagram corresponding to FIG. 2a;

DETAILED DESCRIPTION OF THE PREFERRED EMBODIMENTS

Figure 1:
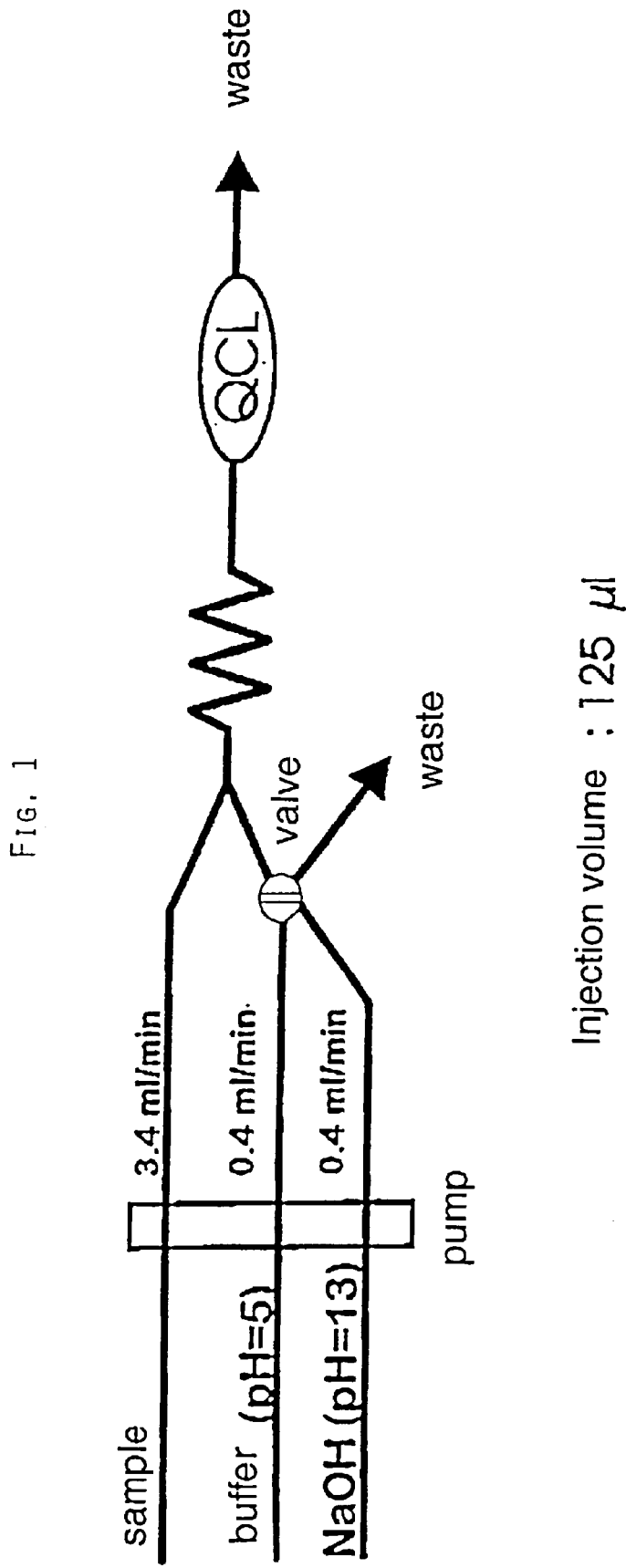
FIG. 1 schematically illustrates an arrangement wherein the preceding modulation is a raising of the pH of the sample.

The present invention will be explained in more detail by way of reference to the figures illustrated in the drawings.

In FIG. 1, an arrangement for the infrared-optical determination of an analyte in a liquid sample by means of a quantum cascade laser (QCL) is illustrated. In this instance, the detection is preceded by a modulation of the analyte, phosphate, i.e. a pH change. The sample is supplied to the detector QCL at a rate of 3.4 ml/min. Upstream of the detector, either a buffer having a pH of 5, or a soda lye having a pH of 13, is mixed with the sample, depending on the valve position.

Figures 2A, 2B:
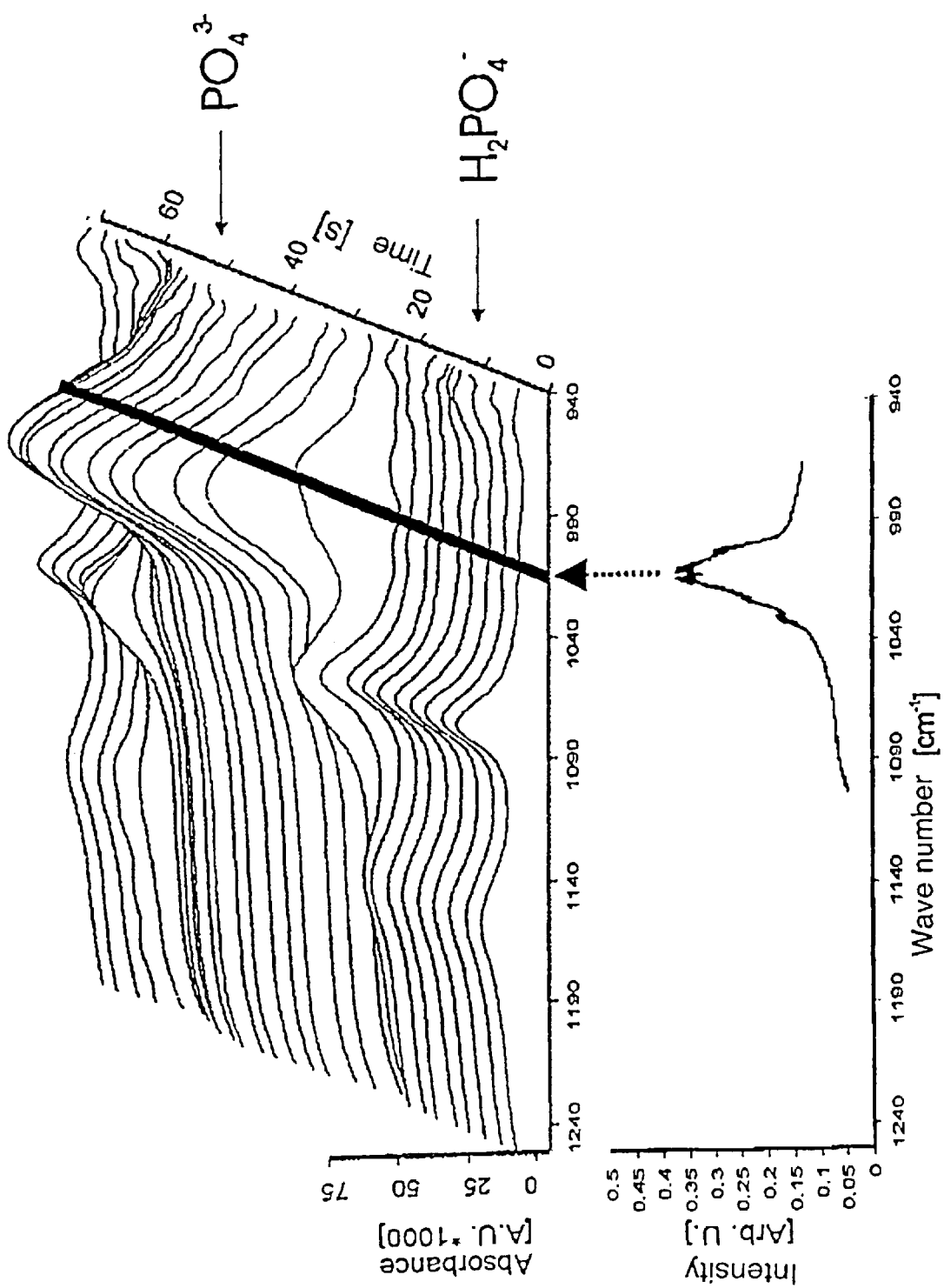
FIG. 2a shows the absorption spectrum of $PO_4^{3-}$ and $H_2PO_4^-$.
FIG. 2b shows the emission spectrum of a quantum cascade laser.

In FIG. 2a it can be seen that the absorption spectrum changes according to the change of the pH. The black bar characterizes the intensity peaks produced by the quantum cascade laser used (see also FIG. 2b). Up to approximately 20 seconds (pH=5), the analyte is present as $H_2PO_4^-$. From about 30 seconds to about 60 seconds, the analyte is present as $PO_4^{3-}$(pH=13). At a pH of 5, less radiation is absorbed, while at a pH of 13, clearly more radiation is absorbed so that a peak forms in this range. Subsequently (after 60 sec), the pH is lowered to pH=5 again, so that the analyte absorbs the radiation to a lesser extent.

Figure 3:
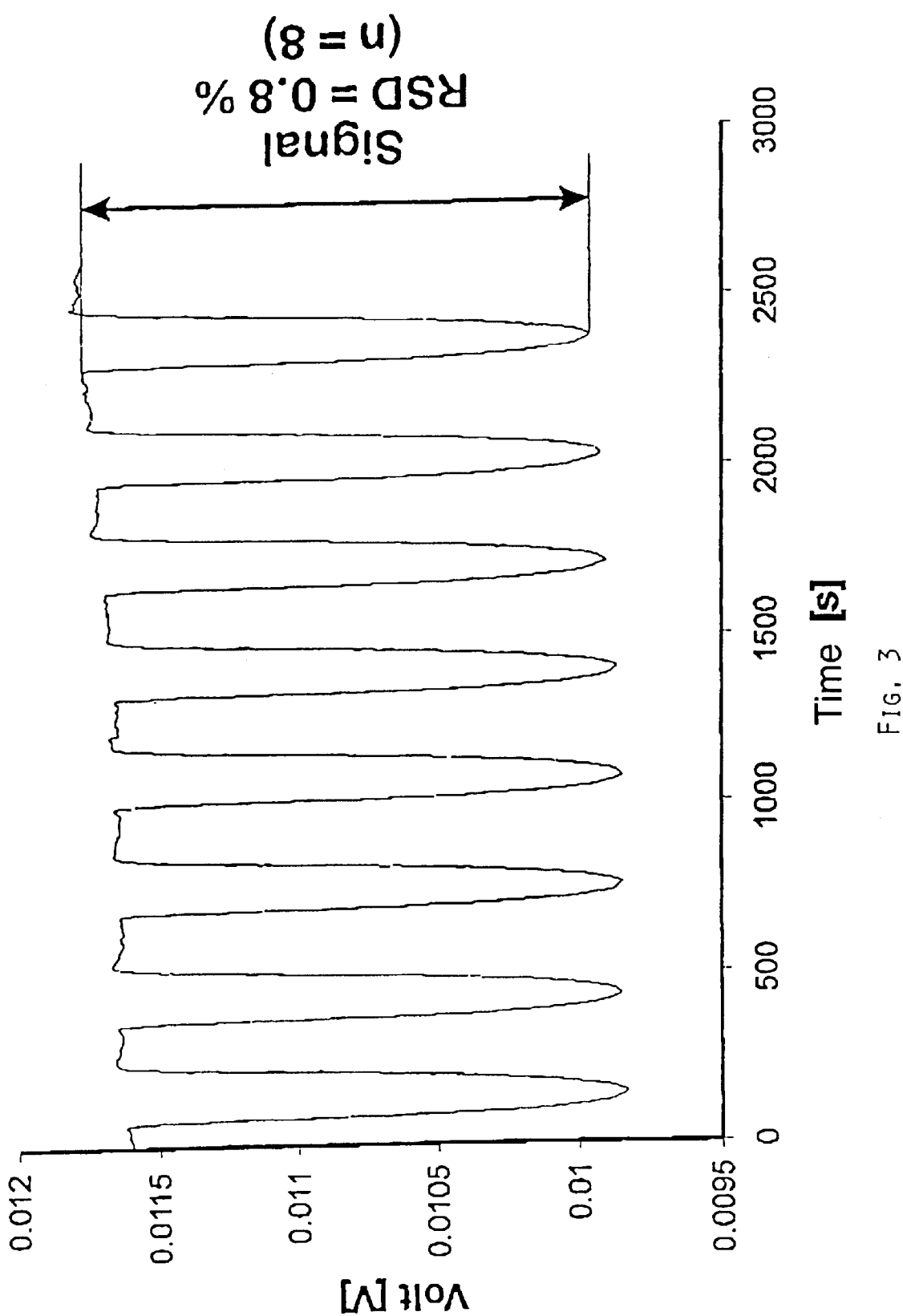

In FIG. 3, the voltage-time diagram corresponding to FIG. 2a is shown. If less radiation is absorbed (pH=5), a maximum voltage of more than 0.0115 V is measured. If the pH is raised to 13 so that the analyte will absorb the radiation to a higher degree, the voltage measured will fall to a minimum of below 0.01 V. Gradually, the pH was changed so that the periodic curve illustrated in FIG. 3 was formed.

Figure 4:
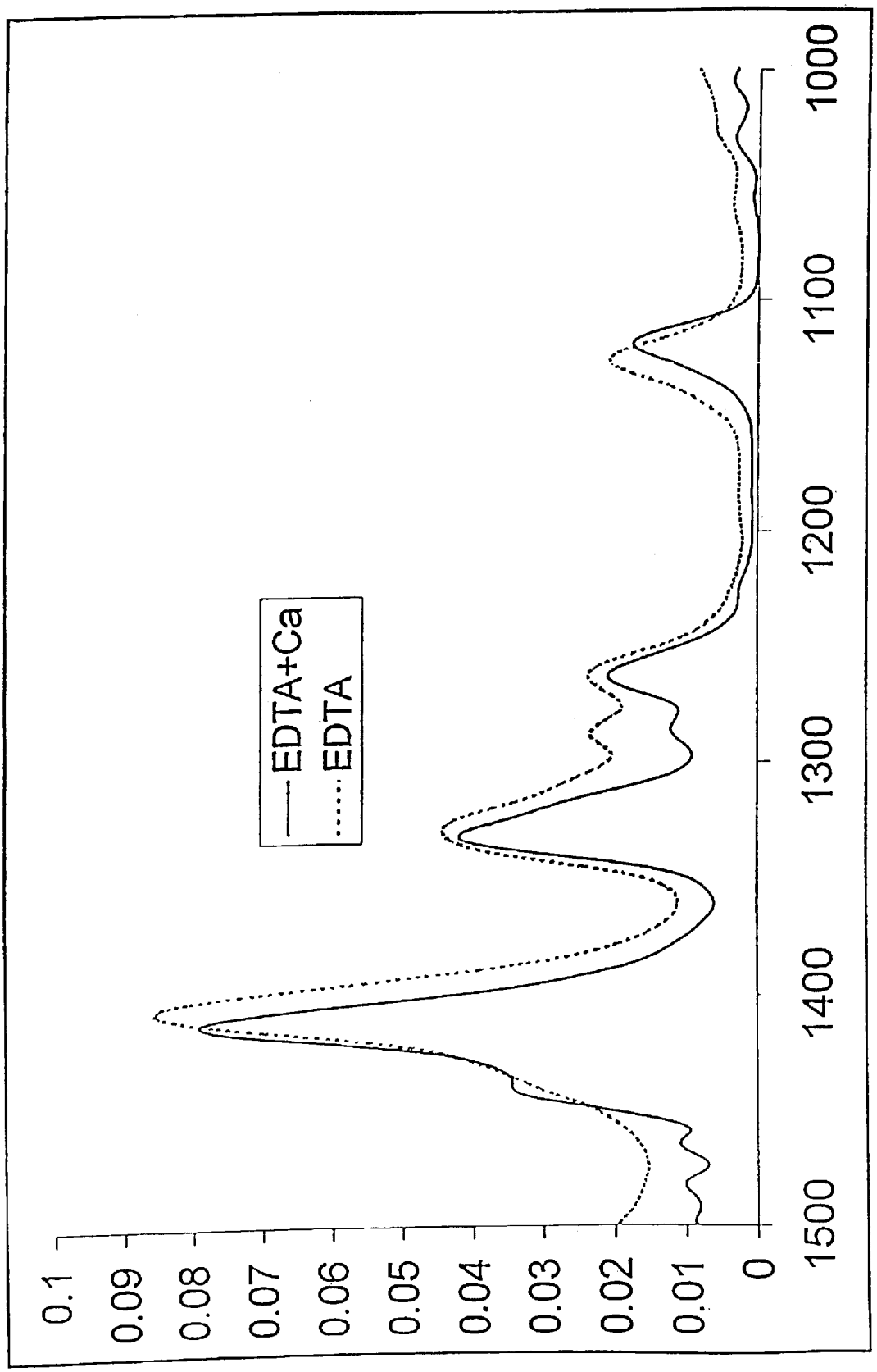
FIG. 4 shows the absorption spectrum of EDTA and EDTA+$Ca^{2+}$.

In FIG. 4, two infrared absorption spectra are illustrated. The absorption measurement can be preceded by a chelating procedure (the absorption spectrum of both the chelation complex EDTA-$CA^{2+}$ and of the EDTA without $Ca^{2+}$ has been illustrated). The differences in peak heights can be precisely determined by means of the quantum cascade laser.

Figure 5:
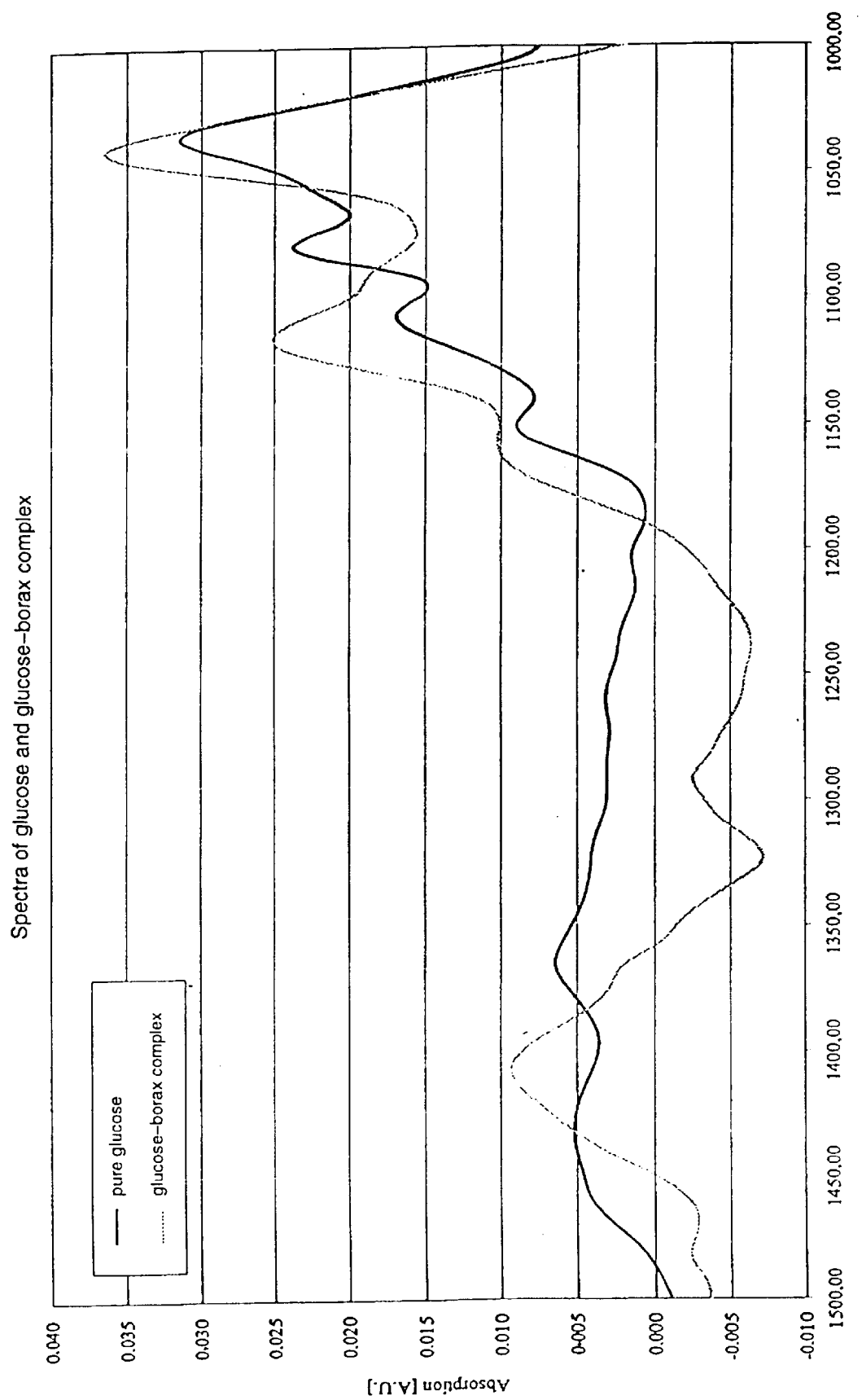
FIG. 5 shows the absorption spectrum of pure glucose and of glucose in the glucose-borax complex.

FIG. 5 also shows two absorption spectra, the modulation preceding detection being a complexing of glucose with borax. The spectrum of pure glucose has other peak intensities than the spectrum of the glucose in the glucose-borax complex, this being precisely measurable when using a quantum cascade laser.

Figure 6:
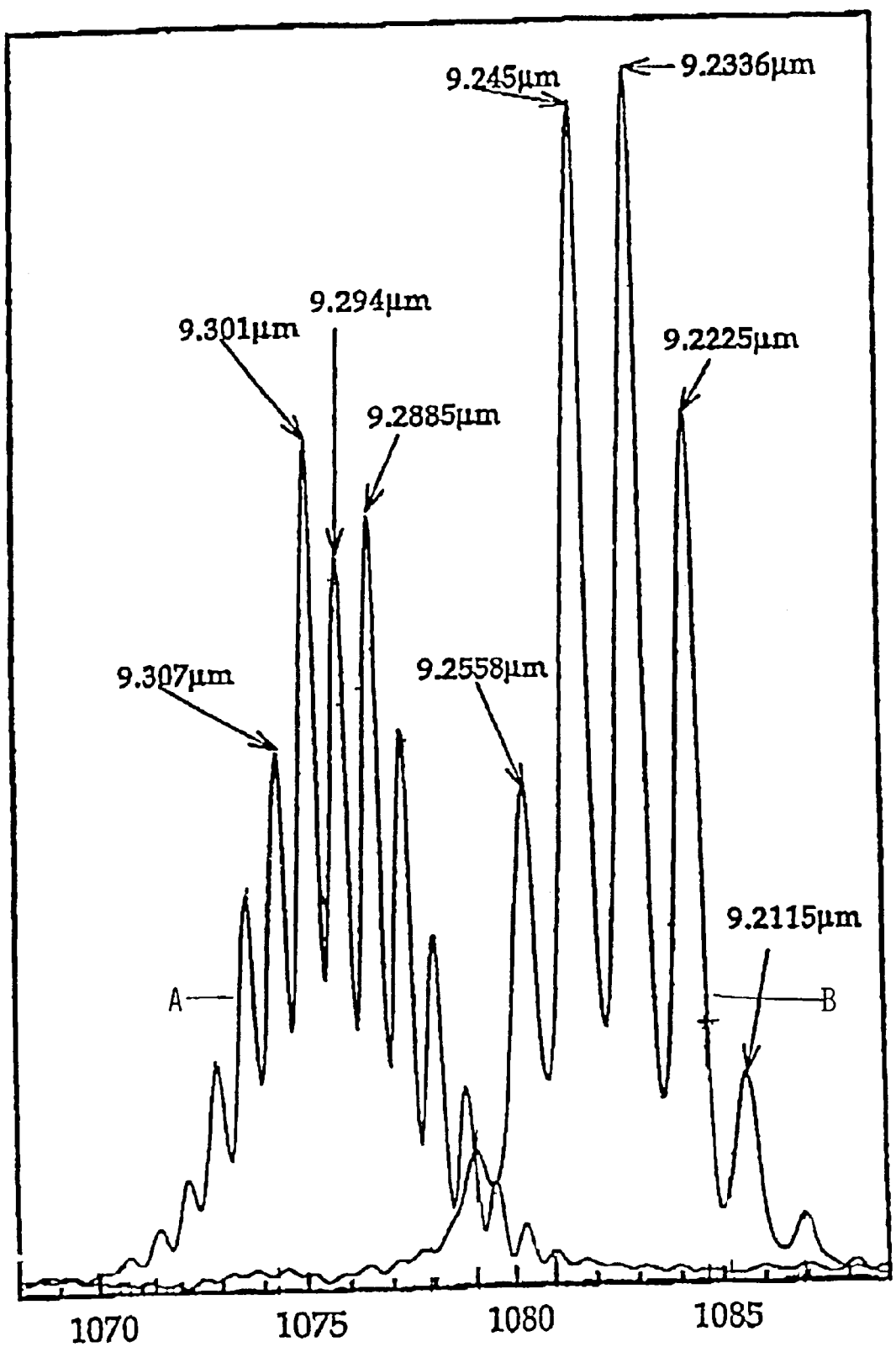
FIG. 6 shows the emission spectra of two quantum cascade lasers.

FIG. 6 shows two emission spectra produced by different quantum cascade lasers A, B. It can be seen that the wavelengths each had sharp intensity peaks, the wavelengths differing by a wavenumber of approximately 1 (0.01 μm). (When using a quantum cascade laser, the peaks are clearly visible, and the measurement becomes sensitive).

Figure 7:
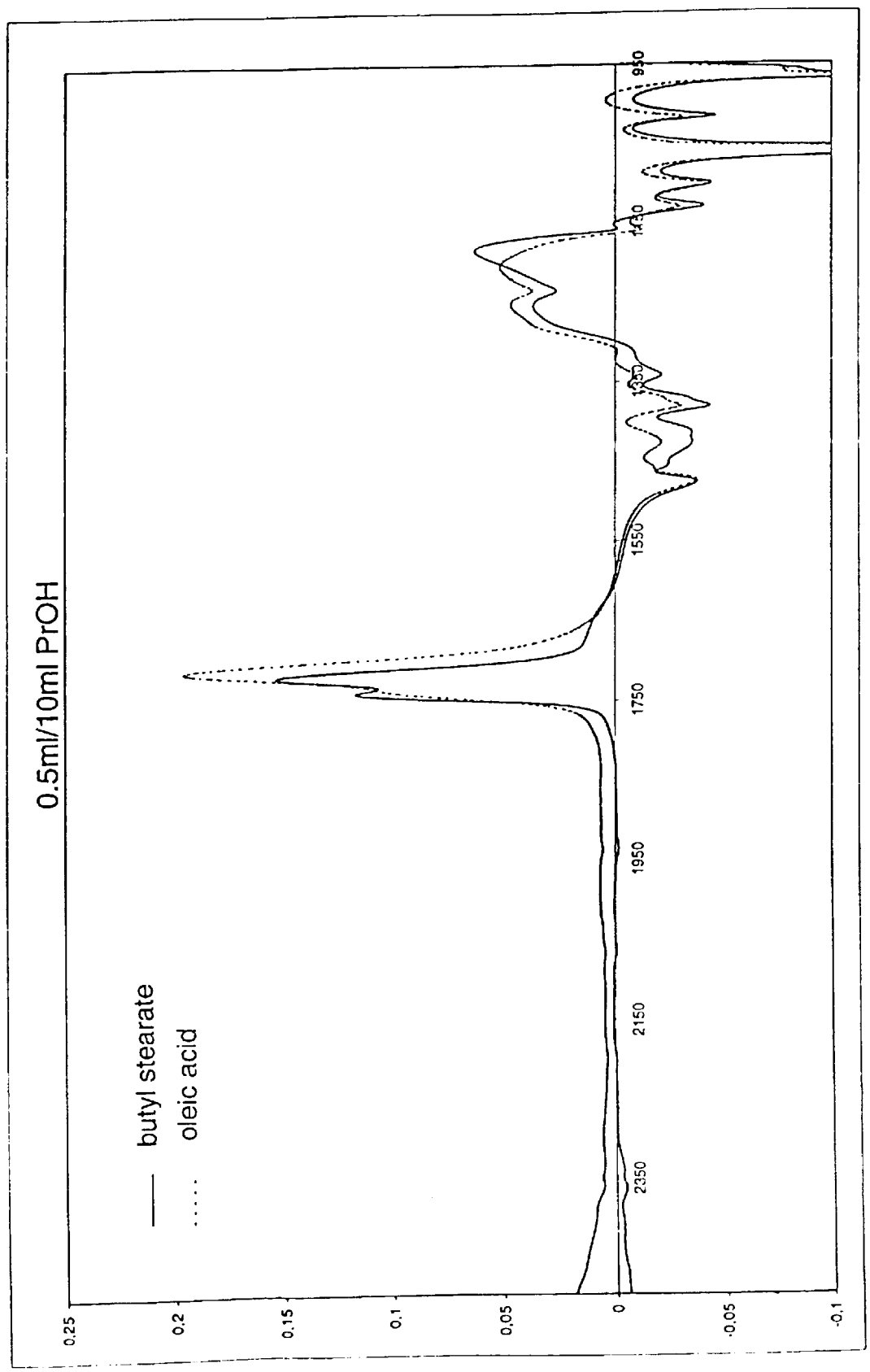
FIGS. 7, 8 and 9 show absorption spectra as obtained in the inventive determination of free fatty acids.

FIG. 7 shows the absorption spectra of a fatty acid ester (butyl stearate) and a free fatty acid (oleic acid) in n-propanol. It can be clearly recognized that the bands of the —C=O stretch oscillation of the two molecules overlap. For a precise determination of the free fatty acid in edible oils which mainly consist of fatty acid esters and secondary components, such as C=O containing compounds like aldehydes and ketones, it is necessary to selectively modulate the absorption spectrum of the free fatty acids.

Figure 8:
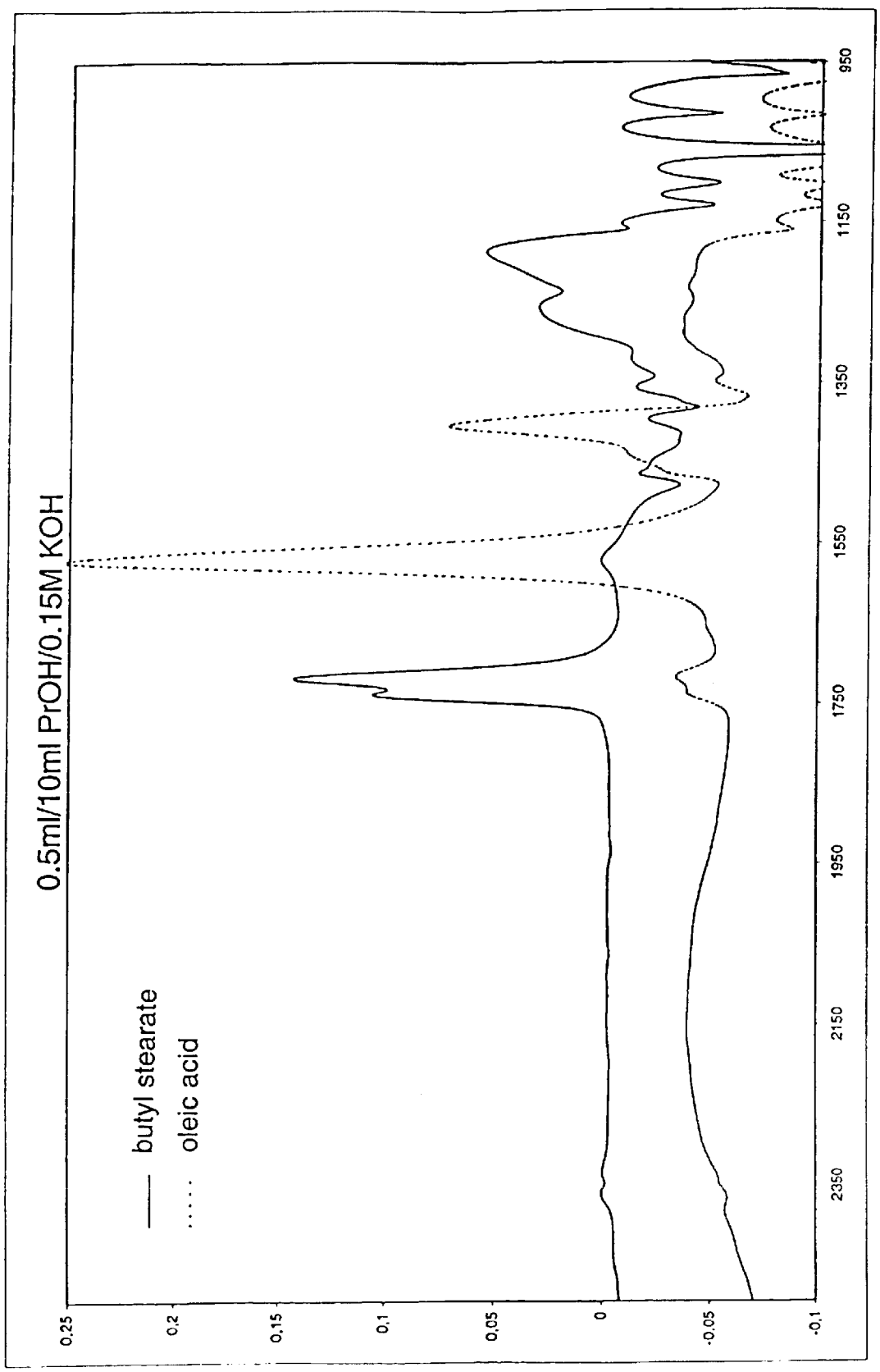

FIG. 8 shows that by adding KOH/n-propanol, the spectrum of the fatty acid ester remains practically unchanged, whereas the spectrum of the free fatty acids changes clearly—the asymmetric stretch oscillation of the carboxylate ion formed is clearly recognizable at 1570 $cm^{-1}$ and the symmetrical stretch oscillation at 1400 $cm^{-1}$. By measuring the infrared absorption of the modulated fatty acid ester spectrum, preferably at 1570 wavenumbers alone or relative to the absorption at 1612 wavenumbers, respectively, with a quantum cascade laser, a precise measurement of the free fatty acid content of edible oils becomes possible.

Figure 9:
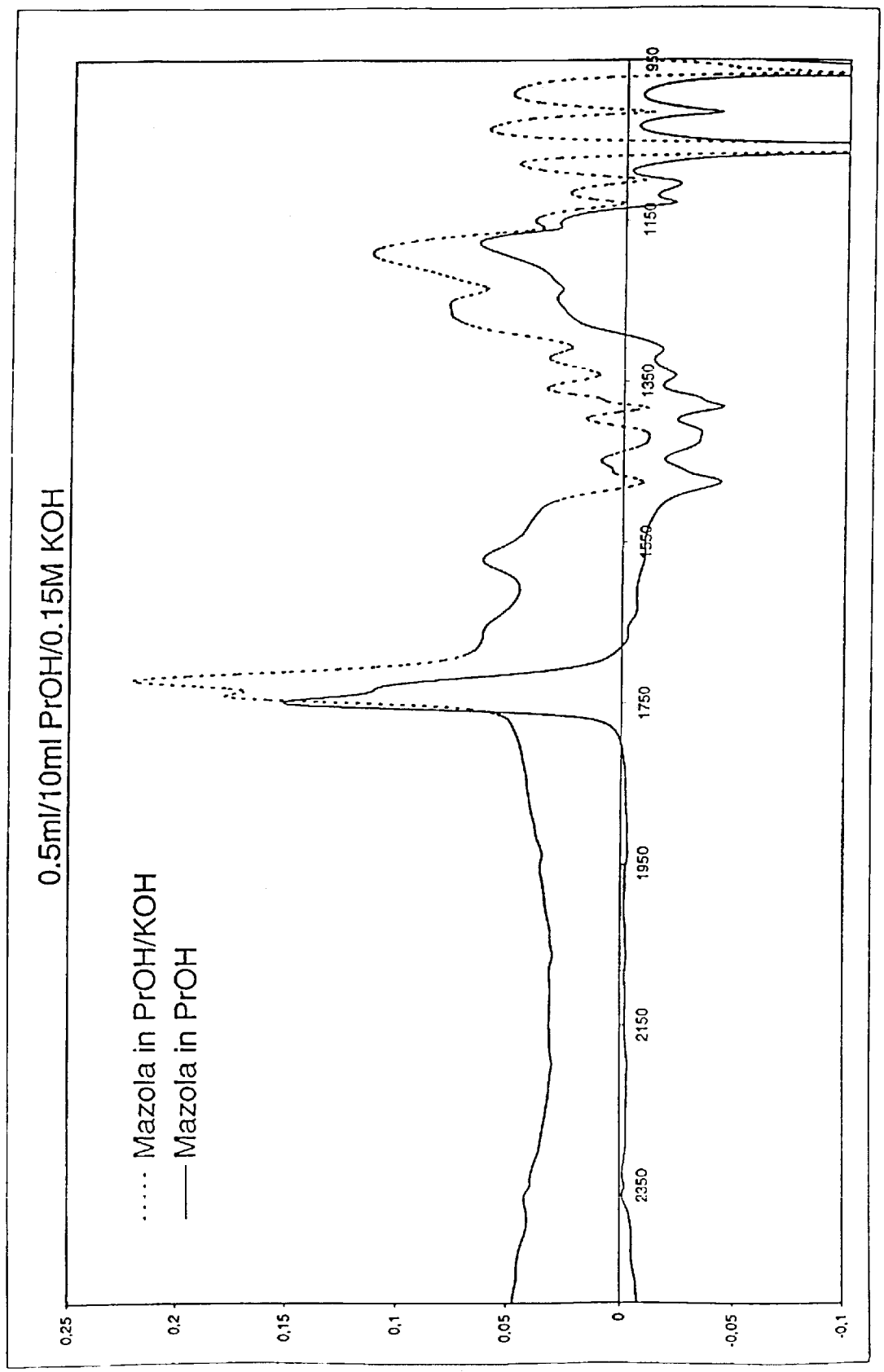

In FIG. 9, a practical example is shown; here, the free fatty acid content of a commercially available edible oil, sold under the trademark Mazola® was determined.

When talking about a "high light density" in the present description, it is meant a spectral power density higher by orders of magnitude than can be attained with conventional thermic radiators, in particular a spectral power density in the range of $10^{-5}$ $W/cm^{-1}$ and more, preferably in the range of $10^{-3}$ $W/cm^{-1}$ and more.

Such infrared radiation with a high power density is produced with a laser, wherein, due to the high spectral density and the sharp intensity peaks with lasers, spectroscopic methods are possible, which cannot be carried out with conventional radiation sources. The combination of infrared spectroscopy with laser spectroscopy results in a method for infrared-optic transmission determination of analytes in a liquid sample, which has a markedly higher sensitivity, flexibility and robustness than conventional methods.

The inventive method may be used to determine concentrations of ions as well as other substances, including organic acids, particularly fatty acids; alcohols; carbohydrates, particularly glucose; proteins; urea; and the like can be measured with high precision.

In phosphate-containing beverages, such as Coca Cola, the pH varies between 2.5 and 3. Thus, in such solutions, both $H_2PO_4^-$ (mostly more than 80%) and $H_3PO_4$ are present. For the direct determination of the entire amount of phosphoric acid, thus, the measurement of both molecules is necessary. This is achieved by measurement of the infrared absorption in several sharp spectral regions, preferably at 1103 cm$^{-1}$, 1078 cm$^{-1}$, 1058 cm$^{-1}$ ($H_2PO_4^-$), 1014 cm$^{-1}$ and 975 cm$^{-1}$ ($H_3PO_4$). The aim of choosing the sharp wavelength regions is to measure the absorption maximums of $H_2PO_4^-$ (1078 cm$^{-1}$) as well as $H_3PO_4$ (1014 cm$^{-1}$) relative to baseline points (1103 cm$^{-1}$, 1058 cm$^{-1}$ and 975 cm$^{-1}$) so that the determination of the total amount of phosphoric acid will not be disturbed by further components such as sodium cyclamate (absorption maximum at 1038 cm$^{-1}$) as well as sugar die (absorption maximum at 1042 cm$^{-1}$) or also a variable water absorption by a change of the pH.

Preferably, the analyte to be measured is additionally subjected to a modulation prior to or during the measurement, wherein changes of the infrared absorption caused by the modulation of the analyte are measured as a function of the analyte concentration to be measured.

By "modulation," any change of the absorption of the sample or of the analyte, is to be understood, such as a chemical reaction or a separation of the sample, respectively, e.g. by means of a chromatographic method. A chemical reaction is, e.g., a change of the pH of the liquid sample so that after the chemical reaction, the analyte will be present in a different form in which it has a characteristic absorption spectrum. For instance, in the concentration determination of phosphate which in the acid region is almost exclusively present in the forms $H_2PO_4^-$ and $H_3PO_4$ (single-charged phosphate or uncharged phosphoric acid), the pH is raised from an acid pH to a pH of more than 13 so that phosphate is almost exclusively present in the triple-charged form. Similarly, the pH can be raised to 9 to 11 so that the phosphate is almost exclusively present in the double-charged form. In the triple-charged form, phosphate has an absorption maximum at a wavenumber of 1005 cm$^{-1}$, and in the double-charged form, the phosphate has an absorption maximum of 1080 cm$^{-1}$.

The term "modulation" also comprehends chelation, wherein the analyte forms a chelation complex with the admixed reagent, the infrared absorption of the complex being measured so that the concentration of the analyte can be precisely determined. In the complexing reaction, EDTA (ethylene diamine tetra-acetic acid)-$Ca^{2+}$-complex or glucose-borax-complex may be used, to mention but two examples. The advantage of such complexing lies in that in a sample comprising alcohols in addition to sugar, low sugar contents can be precisely measured in the presence of high alcohol concentrations by complexing, whereas in a direct, simple infrared-optical determination of the sample, the sugars and the alcohols cannot be determined side by side since the absorption spectra will overlap, as depicted in FIG. 7.

For further possibilities of the technique of modulation, reference is made to the publication by J. Ruzicka "The second coming of flow-injection analysis" (Analytica Chemica Acta, 261 (1992) 3–10).

The term "modulation" also includes the chromatographic separation of sample on a chromatographic column. In this instance, the liquid sample comprising the analyte is chromatographically separated, whereupon the separated sample, when leaving the column, is irradiated with infrared radiation of high light density, the infrared radiation having at least one sharp intensity peak. Each analyte absorbs radiation at a defined wavelength so that the absorption of this determined peak can also be quantitated in case of an incomplete separation.

Furthermore, "modulation" can also mean an interaction between a biological sample (e.g. protein solution, DNA solution, cell cultures etc.) and a certain active substance of a medicament, wherein a possible interaction between the biological sample and the active substance necessarily will be associated with a change of the concentration of the free active substance and a change of the absorption spectrum of the biological sample, respectively.

With the above embodiments of the method of the invention it is, of course, possible also to measure other ions as well as any other substances, such as organic acids, alcohols, carbohydrates, etc., with high precision. The change of the pH will be carried out e.g. by the addition of lye or acid as well as with an ion exchanger. For further embodiments of this method of the infrared-optic determination by means of a chemical reaction, reference is made to the patent specification AT 404,514 B.

When using two or more infrared radiation sources of different wavelengths, the peaks of the respective analyte incompletely separated in chromatographic procedures can be precisely associated, since two or more traces will be taken up at different wavelengths and possible uncertainties in the association of the respective peak can be eliminated by comparing the traces (thus, different analytes can absorb in one trace, yet not in the other ones, and vice versa, cf. also Journal of Chromatography, A824 (1998) 159–167).

Preferably, the infrared radiation is produced by means of at least one laser. In this manner, the maximum light density and the best resolution can be obtained. The adjustments of the laser will depend on the desired wavelength range.

In principle, any type of laser can be used for producing infrared radiation, such as diode laser, dye laser, color center laser, to mention but a few examples. For the method according to the invention it is important that the lasers produce practically monochromatic light. This ensures that a spectrum having one or more sharp peaks with closely adjacent wavelengths is obtained in the desired wavelength range. If an analyte in the sample absorbs radiation at a very distinct wavelength, the concentration of this substance will clearly be detected even at a very low concentration.

Moreover, an advantage of lasers, in contrast to thermic radiators, is that lasers can be operated effectively by pulsing, thus resulting in a higher modulation depth will result.

In diode lasers, a current is sent through a p-n semiconductor diode in transmission direction so that electrons and holes will recombine in the region of the p-n transition. The end faces of the diode in most instances act as a resonant mirror. Diode lasers do not have a definite wavelength.

Color center lasers are solid lasers in which a crystal with color centers is used as the active medium. With various crystals they cover the entire range of the near infrared wave range of from 0.8 to 4 μm.

Dye lasers are lasers whose active medium consists of organic dyes dissolved in liquids. The dyes have wide emission bands.

A further suitable method of the present invention results in that when several lasers are used, the mean values of the respective intensity peaks of the infrared radiation differ from each other by about 50 wavenumbers. The lasers generate radiation, which is tunable in a range of approximately 40 to 50 wavenumbers. If two lasers are used which generate radiation whose wavelengths differ by 50 wavenumber, these two lasers will cover a range of approximately 100 wavenumbers. The more lasers used, the larger the wavenumber range that can be covered.

A particularly preferred embodiment is a method where several sharp intensity peaks in one laser emission spectrum differ from one another by about 1 wavenumber (0.01 micrometer). This difference allows for a highly specific determination of even minute amounts of an analyte, since the absorption of a single absorption band can be precisely detected and quantitated. Such emission spectra can only be produced with lasers. Conventional infrared light sources (i.e., thermic radiators with a filter), are only capable of producing wavelength ranges of approximately 20 wavenumbers, which ranges differ by approximately 20 to 50 $cm^{-1}$.

It is also suitable if the infrared radiation is produced by several lasers. Each laser has a specific emission spectrum, and it thus becomes possible to cover any desired wavelength range. The lasers to be used will be selected depending on which wavelengths are absorbed by the analytes to be determined.

Preferably, a method is used wherein the lasers are quantum cascade lasers. A quantum cascade laser is a semiconductor laser which uses only one type of carrier and which is based on the principle of quantum restriction. In a quantum cascade laser, the electrons make the transitions between restricted conditions in ultra-thin alternating layers of a semiconductor material. The emission wavelength then will depend on the thickness of the layers so that a wide spectrum of mean infrared wavelengths far into the remote infrared region can be produced, in particular between 3.5 and 17 $\mu$m. A particular advantage of the quantum cascade laser is the possibility of higher operating temperatures. The disadvantage of nearly all diode lasers is the high current density, which, when reached without cooling, would lead to a thermal breakdown. The efficiency of cooling in this zone restricts the discharge current and thus the light power of the diode laser. On the other hand, quantum cascade lasers may be used at and above room temperature, which, until now, had not been possible. Since the quantum cascade laser is based on a cascade of identical conditions (typically from 20 to 50), an electron will emit many photons so that a higher optical power will be emitted. A further advantage of the quantum cascade laser lies in its increased robustness. The foregoing advantages establish that the method according to the present invention for the infrared-optic determination of the concentration of at least one analyte in a liquid sample, wherein the infrared radiation is produced by means of a quantum cascade laser, is specific, rapidly feasible, and optimal for industrial application.

In any event, it is particularly advantageous if the lasers of the present invention are designed to be tunable, that is, the wavelength of the laser can be changed in a controlled manner. Use of a tunable laser in an infrared-optical determination makes the method much more flexible. In this manner it becomes possible to use a single device for determining all types of analytes, complexes, molecules etc., a device that can be adapted to a wide variety of chemical analyses. With diode lasers, the wavelength is tunable in a range that depends on the semiconductor material used, and the tuning is effected by changing the temperature and/or the discharge current. Tunable diode lasers deliver light in the near, middle, and far infrared between 0.8 and 32 $\mu$m.

The inventive arrangement is characterized in that at least one laser is provided as the radiation source for the infrared radiation, the laser produces a radiation of high light density, and the infrared radiation has a sharp intensity peak at one or more wavelengths. The arrangement can be constructed such that an on-line measurement, e.g. on a living patient with a return of the sample to the patient is possible. Thus, an arrangement is provided which has a simple structure and allows for a rapid and specific determination of analytes.

Preferably, in the arrangement according to the invention, furthermore the sample cuvette is preceded by a modulation device, or the sample cuvette includes a modulation device, in which the analyte can be influenced in a manner that changes its absorption behavior.

A particularly preferred arrangement is comprises at least one laser that is a quantum cascade laser, which produces infrared radiation having at least one sharp intensity peak. As has already been described above, this will allow for an extremely precise determination of analytes.

Advantageously, an embodiment of the present invention is characterized in that the at least one quantum cascade laser produces infrared radiation whose intensity peaks will differ by a wavenumber of approximately 1 (0.01 micrometer). This embodiment allows the precise measurement of the analyte, since a high light intensity in the range of the infrared absorption band of the analyte is attained.

A preferred embodiment is arrangement wherein, when several lasers are used, the mean values of the respective intensity peaks of the infrared radiation will differ from each other by a wavenumber of approximately 50.

Particularly preferred is an arrangement in which the laser(s) is (are) designed to be tunable.

Furthermore, the present invention relates to the use of a quantum cascade laser as an infrared radiation source for the infrared-optical determination of the concentration of at least one analyte in a liquid sample.

Additional advantages and modifications will readily occur to those skilled in the art. Therefore, the invention in its broader aspects is not limited to the specific details and illustrative embodiments shown and described herein. Accordingly, various modifications may be made without departing from the spirit or scope of the general inventive concept as defined by the appended claims and their equivalents.

What is claimed is:

1. A method of infrared-optically determining a concentration of at least one analyte in a liquid sample, comprising
    irradiating said liquid sample with an infrared radiation of high light density, said infrared radiation having a sharp intensity peak at at least one wave length,
    measuring the infrared absorption of the at least one analyte, and
    comparing said infrared absorption measured with a standard
wherein said infrared radiation is produced by at least one laser that is tunable in a wave number range of at least 40.

2. A method as set forth in claim 1, further comprising
    subjecting said at least one analyte to be measured to a modulation so as to induce a change in the infrared absorption of said at least one analyte, and
    measuring said induced change of said infrared absorption of said at least one analyte as a function of said concentration of said analyte to be determined.

3. A method as set forth in claim 2, wherein said at least one analyte is subjected to said modulation prior to said measuring of said infrared absorption.

4. A method as set forth in claim 2, wherein said at least one analyte is subjected to said modulation during said measuring of said infrared absorption.

5. A method as set forth in claim 1, wherein several lasers are used producing infrared radiation having respective intensity peaks, mean values of said respective intensity peaks differing from each other by a wave number of approximately 50.

6. A method as set forth in claim 1, wherein several sharp intensity peaks are provided in an emission spectrum of said at least one laser, said sharp intensity peaks differing from each other by a wave number of approximately 1 (0.01 micrometer).

7. A method as set forth in claim 6, wherein said at least one laser is designed as a quantum cascade laser.

8. A method of infrared-optically determining concentration of at least one analyte in a liquid sample, comprising subjecting said liquid sample containing said analyte to an infrared radiation of high light density, said infrared radiation having a sharp intensity peak at at least one wavelength, subjecting said at least one analyte to be measured to a modulation so as to induce a change of infrared absorption in said at least one analyte, and measuring said changed infrared absorption of said at least one analyte as a function of the concentration of said at least one analyte to be determined, and comparing said infrared absorption measured with a standard.

9. A method as set forth in claim 8, wherein said at least one analyte to be measured is subjected to said modulation prior to said measuring of said infrared absorption.

10. A method as set forth in claim 8, wherein said at least one analyte to be measured is subjected to said modulation during said measuring of said infrared absorption.

11. An arrangement for an infrared-optical transmission determination of a concentration of at least one analyte in a liquid sample, said arrangement comprising a radiation source having the form of at least one laser being tunable in a wave number range of at least 40 for providing an infrared radiation of high light density, said infrared radiation having a sharp intensity peak at at least one wave length, a sample cuvette flowed through by said sample liquid containing said at least one analyte, and an infrared absorption detector, said sample cuvette with said sample liquid containing said at least one analyte being disposed between said radiation source and said detector so as to be passed through by said infrared radiation of high light density, and said infrared absorption detector measuring the infrared absorption induced by said at least analyte in said sample cuvette.

12. An arrangement as set forth in claim 11, further comprising a modulation device, said at least one analyte having a certain infrared absorption behavior, and said modulation device being capable of influencing said analyte so as to change said infrared absorption behavior of said at least one analyte.

13. An arrangement as set forth in claim 12, wherein said modulation device precedes said sample cuvette.

14. An arrangement as set forth in claim 12, wherein said modulation device is contained in said sample cuvette.

15. An arrangement as set forth in claim 11, wherein at least one of said lasers is designed as a quantum cascade laser producing an infrared radiation with at least one sharp intensity peak.

16. An arrangement as set forth in claim 15, wherein said at least one quantum cascade laser produces an infrared radiation having intensity peaks differing from each other by approximately 1 wave number (0.01 micrometer).

17. An arrangement as set forth in claim 11, wherein several lasers are used, mean values of said intensity peaks of said infrared radiation emitted by said lasers differing from each other by a wave number of approximately 50.

* * * * *

UNITED STATES PATENT AND TRADEMARK OFFICE
CERTIFICATE OF CORRECTION

PATENT NO. : 6,737,651 B1
DATED : May 18, 2004
INVENTOR(S) : Lendl

It is certified that error appears in the above-identified patent and that said Letters Patent is hereby corrected as shown below:

Title page, Item [54] and Column 1, line 3,
Title, after "LIQUID", insert -- SAMPLE --.

Column 9,
Line 13, after "determining", insert -- a --.

Signed and Sealed this

Twenty-first Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,737,651 B1  Page 1 of 1
APPLICATION NO. : 09/958248
DATED : May 18, 2004
INVENTOR(S) : Lendl It is certified that error appears in the above-identified patent and that said Letters Patent is hereby corrected as shown below:

On the Title Page, Section [73], Assignee, please add a second Assignee as follows:

--Bernhard Lendl, Vienna, AT--.

Signed and Sealed this

Fifteenth Day of August, 2006

JON W. DUDAS
*Director of the United States Patent and Trademark Office*